United States Patent [19]
Nichter

[11] Patent Number: 6,110,174
[45] Date of Patent: Aug. 29, 2000

[54] METHOD OF FIXATING BONE BY DRIVING A WIRE THROUGH OSCILLATION

[75] Inventor: Larry S. Nichter, 71 Fremont Pl., Los Angeles, Calif. 90005

[73] Assignee: Larry S. Nichter, Huntington Beach, Calif.

[21] Appl. No.: 08/185,221

[22] Filed: Jan. 24, 1994

Related U.S. Application Data

[63] Continuation of application No. 07/898,120, Jun. 12, 1992, abandoned.

[51] Int. Cl.[7] ............................. A61B 17/68; A61B 17/88
[52] U.S. Cl. ............................. 606/72; 606/103; 606/104
[58] Field of Search .................... 606/72, 73, 96, 606/102–105

[56] References Cited

U.S. PATENT DOCUMENTS

| | | | |
|---|---|---|---|
| 2,081,293 | 5/1937 | Davis | 606/73 X |
| 2,143,922 | 1/1939 | Longfellow | 606/73 X |
| 2,831,132 | 4/1958 | Jackson | 310/26 |
| 3,214,776 | 11/1965 | Bercouitz | 15/26 |
| 3,640,280 | 2/1972 | Slanker et al. | 128/317 |
| 4,111,208 | 9/1978 | Leuenberger | 606/179 X |
| 4,298,074 | 11/1981 | Mattehen | 606/104 X |
| 4,306,570 | 12/1981 | Matthews | 606/179 X |
| 4,341,206 | 7/1982 | Perrett et al. | 606/180 X |
| 4,353,422 | 10/1982 | Benett, Jr. | 172/41 |
| 4,355,931 | 10/1982 | Leuenberger | 606/168 X |
| 4,373,518 | 2/1983 | Karser et al. | 606/72 |
| 4,383,527 | 5/1983 | Asnis et al. | 128/926 B |
| 4,399,813 | 8/1983 | Barber | 128/92 EC |
| 4,409,973 | 10/1983 | Neufeld | 606/179 X |
| 4,419,904 | 12/1983 | Albury | 74/44 |
| 4,441,563 | 4/1984 | Walton, II | 606/104 X |
| 4,458,374 | 7/1984 | Hukuba | 15/22 |
| 4,498,468 | 2/1985 | Hansson | 128/92 B |
| 4,541,422 | 9/1985 | de Zbikowski | 606/73 X |
| 4,596,243 | 6/1986 | Bray | 606/178 X |
| 4,955,888 | 9/1990 | Slocum | 606/178 X |
| 4,978,350 | 12/1990 | WayenKnecht | 606/72 |
| 5,139,499 | 8/1992 | Small et al. | 606/73 |

*Primary Examiner*—Danton D. DeMille
*Attorney, Agent, or Firm*—Whitham, Curtis & Whitham

[57] ABSTRACT

A method and/or apparatus is provided for bone fixation which includes oscillating a wire about a longitudinal axis, advancing the oscillating wire into the bone tissue, and leaving the wire in the bone tissue as a fixation element. The apparatus in the present invention may be a self-contained unit for providing oscillatory motion to a chuck configured for releasably engaging a K-wire or the like, or may include a drive gear for use with a conventional rotor and drill for accomplishing the same oscillatory action.

5 Claims, 3 Drawing Sheets

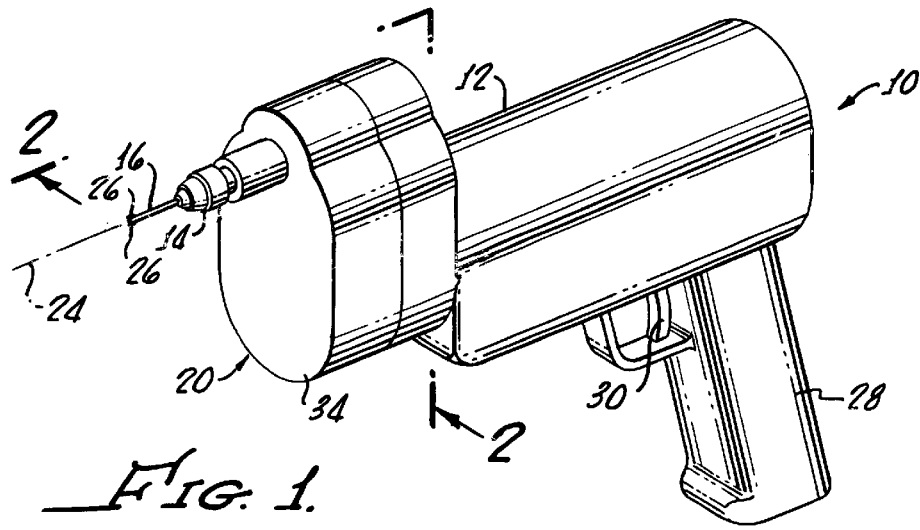
FIG. 1.
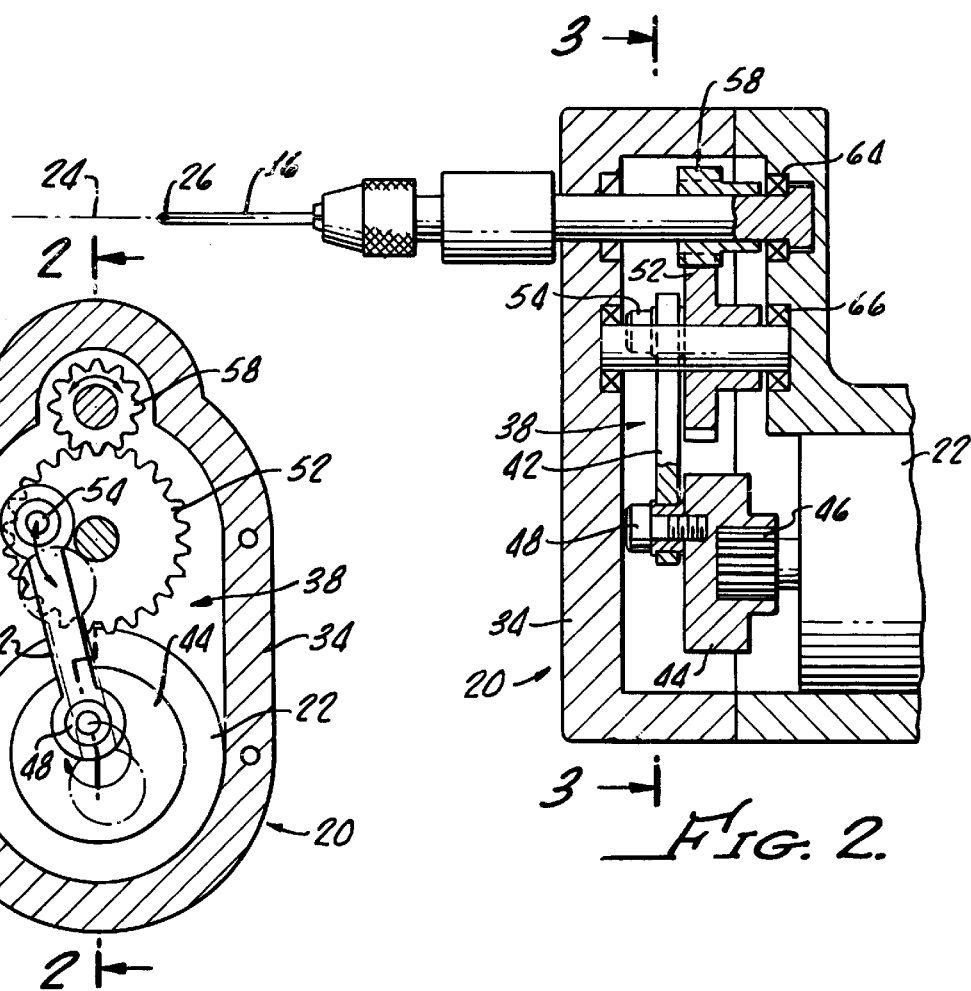
FIG. 2.
FIG. 3.

MEAN PEAK INSERTIONAL FORCE

MEAN PEAK PULL OUT FORCE

6,110,174

METHOD OF FIXATING BONE BY DRIVING A WIRE THROUGH OSCILLATION

This application is a continuation of application Ser. No. 07/898/120, filed Jun. 12, 1992 now abandoned.

The present invention generally relates to instruments for driving a fixing means into bone tissue and is more particularly directed to a wire driver for use in the field of surgery.

Heretofore, wires such as Kirschner wires (K-wires), and/or pins, have been inserted into bone tissue using a traditional rotary drill. However, nearby vascular, nerve and tendon damage often occurs through the use of a traditional rotary drill.

This is particularly true when working with delicate critical structures of the hand or foot and is most important in replantation surgery where bone fixation occurs in the midst of several loose neurovascular and tendinous structures, many of which are "tagged" with sutures. In these cases, the "wrapping" action of the rotary drill tends to cause additional traction or avulsion injury to contacting soft tissues. This problem is increased when multiple K-wires are utilized in either a crossed or intraosseous confirmation, which has been shown to improve the stability of fixation for both phalangeal and metacarpal injuries.

Thus, there is a need for a drilling instrument for driving wires which decreases the possibility of iatrogenic soft tissue damage. Such a device would be most -useful in the treatment of hand and foot fractures. In hand surgery, for example, phalangeal, metacarpal, and carpal fractures occur in great frequency; and rigid, internal fixation in conjunction with either open or closed reduction is the method of treatment most popularly used.

The present invention overcomes the shortcomings of heretofore rotary drills and provides for an instrument and method in which a K-wire, or pin, is oscillated during advancement into a bone.

SUMMARY OF THE INVENTION

In accordance with the present invention, a method for bone fixation includes the steps of oscillating a wire about a longitudinal axis, advancing the oscillating wire into the bone tissue, and thereafter leaving the wire in the bone tissue as a fixation element. More particularly, the method of the present invention includes advancement of the oscillating wire through surrounding soft tissue without the possibility of risk of wrapping surrounding soft tissue about the oscillating wire. In other words, the oscillating wire may be advanced through surrounding soft tissue without traction and/or avulsion injury to the surrounding soft tissue. As a specific example, no histopathological changes in arteries are observed when an oscillating wire, in contact with a vessel, is passed at about 1,200 oscillations per minute as compared to the marked histopathological changes and vascular spasms occurring with a wire rotated at an equivalent speed.

Importantly, the method of the present invention includes the advancement of the oscillating wire into the bone with less force than is required for the advancement of the wire when the wire is rotated at a speed equal to the oscillation frequency of the wire. As a specific example, the wire may be oscillated at about 1,200 oscillations per minute during advancement into bone tissue, utilizing an average of 3 newtons less force than required by a conventional rotary drill operating at a similar number of rpms.

A device in accordance with the present invention generally includes housing and chuck means for releasably gripping one end of a Kirschner-type wire. Drive means are provided and disposed in operative engagement with the chuck means for oscillating the chuck means about a longitudinal axis thereof. The drive means may be configured for releasably engaging a rotary power source. Alternatively, the drive means for oscillating the chuck means may be incorporated into the housing with a motor in operative engagement therewith. A suitable means for oscillating the chuck means may comprise a pitman-type drive.

BRIEF DESCRIPTION OF THE DRAWINGS

The advantages and features of the present invention will appear from the following description when considered in conjunction with the accompanying drawings in which:

FIG. 1 is a perspective view of a wire driver in accordance with the present invention generally showing housing and a chuck for releasably gripping one end of a Kirschner-type wire;

FIG. 2 is a cross-sectional view taken along the line 2—2 of FIG. 1, showing a transverse cross-sectional view of a Pitman-type drive for oscillating chuck;

FIG. 3 is a front cross-sectional view taken along the line 3—3 of FIG. 2, showing the Pitman-type drive.

DETAILED DESCRIPTION

Figure 4:
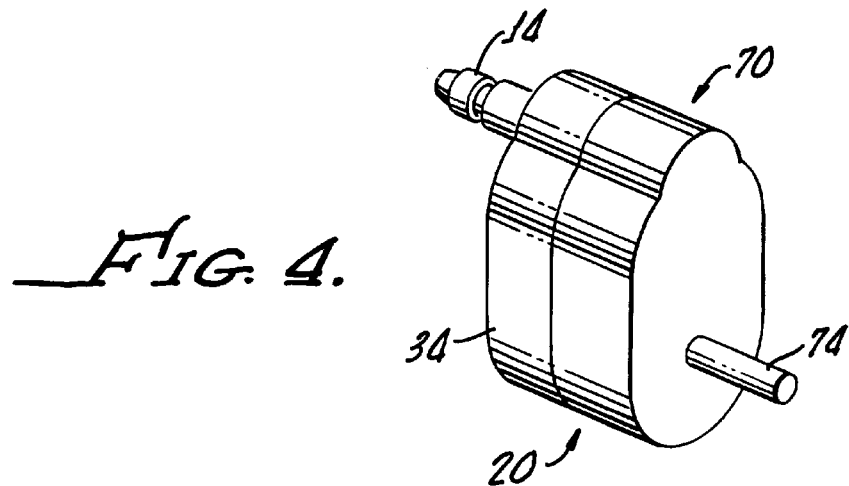
FIG. 4 is an alternate embodiment of the present invention showing a perspective view of a drive unit suitable for use with a conventional rotary drill.

Turning now to FIG. 1, there is shown a wire driver 10, in accordance with the present invention, which generally includes a housing 12, a chuck 14, which provides means for releasably gripping one end of a Kirschner-type wire 16 and a gear drive 20, interconnecting a motor 22 (see FIG. 2) and the chuck 14, for oscillating the chuck 14 about a longitudinal axis 24. Pins or wires, such as the Kirschner-type wire 16, have a number of bezels, or cutting edges 26 thereon to facilitate advancement, or drilling, of the wire into bone tissue.

The housing 12 may have any conventional shape and may include a pistol grip 28 which provides means for enabling a manual holding and positioning of the wire driver 10. A conventional trigger switch 30 may be provided for controlling power to the motor 22 in a conventional manner.

Turning now to FIGS. 2 and 3, the gear drive 20 may include any convenient housing 34 for enclosing a Pitman-type drive 38 for converting the rotary motion of the motor 22 to the desired oscillatory movement of the chuck 14.

As shown in FIGS. 2 and 3, the Pitman-type drive 38 generally includes a drive rod 42 rotatably attached to a drive gear 44, engaging a motor gear 46. The drive rod 42 is mounted to the drive gear 44 by a pin 48 in a non-coaxial relationship with the motor gear 46. This causes translational movement of the drive rod, which is interconnected to an intermediate gear 52 by means of a pin 54 in a geometric configuration such that rotation of the motor gear 46 causes reversible, partial rotation of the intermediate gear 52. The chuck gear 58 is sized and interconnected with the chuck 14 by means of a shaft 16 such that one revolution of the motor gear 46 provides a preset reversible oscillatory movement of the chuck 14. All of the gears in the Pitman-type drive 38 are suitably mounted in bushings 64, 66 for translating the rotational movement of the motor gear 46 to an oscillatory movement of the chuck 14. It has been found that the arc over which the oscillation occurs should be at least equal to, and preferably just greater than, 360 degrees divided by the number of bezels, or cutting edges, 26 on the wire 16.

Typically, K-wires are available with two to four cutting edges 26 and accordingly, the corresponding preferable arc of oscillation is equal to just greater than 180 degrees, 120 degrees and 90 degrees, respectively. This provides the optimum cutting efficiency for the advancing wire 16. In addition, in the embodiment in which the motor and means for oscillating the chuck means are disposed within the housing, the housing itself may include pistol grip means for enabling the manual holding and positioning of the wire driver.

An alternative embodiment 70 of a wire driver, in accordance with the present invention, is shown in FIG. 4. This embodiment 70 is identical in mechanical configuration to the gear drive 20 shown in FIGS. 1 to 3, except that the drive gear 44 is configured with a shaft 74 suitable for engagement with a conventional-type rotary drill. The cross-sectional views of the gear drive 20, shown in FIGS. 2 and 3 are identical in this embodiment 70 and therefore are not repeated.

Figure 5:
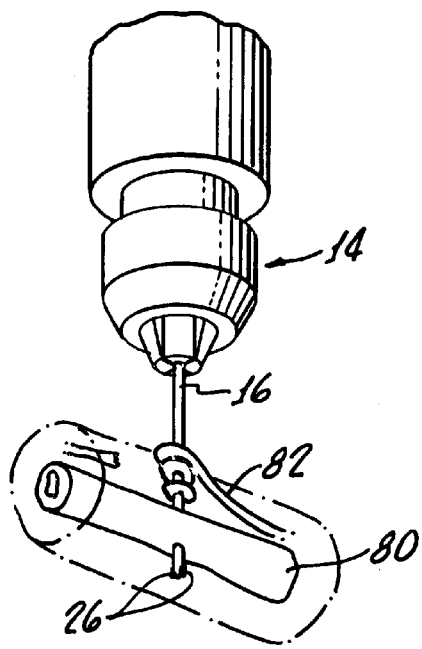
FIG. 5 is a perspective view of a representation showing the use of a prior art rotary drill, causing the "wrapping" action thereof on soft tissue.
Figure 6:
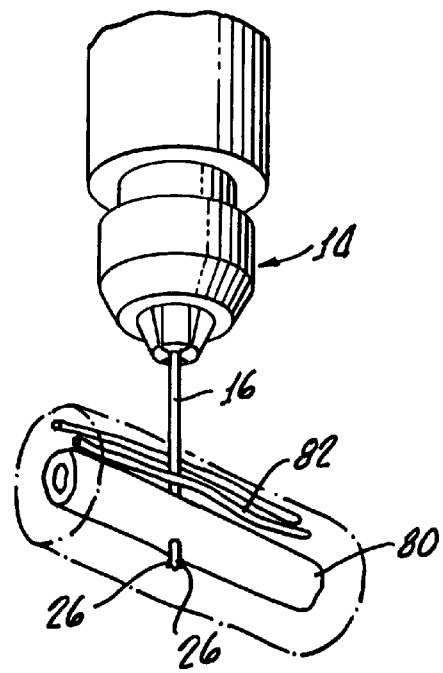
FIG. 6 is a representation similar to that shown in FIG. 5 utilizing the driver of the present invention for advancing a wire through a bone with little or no damage to adjacent soft tissue.

A method for bone fixation in accordance with the present invention generally includes steps of oscillating a wire 16 about a longitudinal axis and advancing the oscillating wire 16 into bone tissue 80, as depicted in FIG. 6. Thereafter, the wire 16 is left in the bone tissue 80 as a fixation element. Importantly, the method in accordance with the present invention encompasses the advancement of the wire 16 through surrounding soft tissue 82 without wrapping of the surrounding soft tissue 82 about the oscillating wire 16 as shown in FIG. 6. This should be contrasted with the prior art devices represented in FIG. 5, in which a conventional rotary drill causes significant damage by way of wrapping of soft tissue as the wire 16 is advanced into the bone tissue 80.

Further, as hereinafter shown, less force is required utilizing the method of the present invention as is necessary for the advancement of the wire when the wire is rotated in accordance with the prior art, at a speed equal to the oscillation frequency of the wire 16. The oscillation frequency may be varied and is dependent upon many factors. However, it has been found that when the wire is oscillated at about 1200 oscillations per minute during advancement into the bone tissue, successful fixation may be obtained.

It has heretofore been thought that the most common complications arising from insertion wires for external or internal extremity skeletal fixation are the direct result of thermal necrosis to bone and soft tissue by the heat generated from the process of wire insertion.

The thermal damage incurred by bone and soft tissue is known to be a function of the maximum temperature of the tissue and the length of time that the tissue is subjected to the damaging temperature. Temperature elevation is a significant clinical problem such that numerous methods have been developed for reducing the temperature generated by power drills with such methods including pre-drilling, the use of hand drills, the development of different wire point designs and various techniques for saline irrigation. See N. Jacob, et al., and L. S. Matthews, et al. who have shown that in hand and rotary power drills, thermal necrosis is related to both high rotational velocities and increased applied force while inserting the wires ("A Study of the Bone Machining Process-Drilling," *Journal of Biomechanics,* 9:343, 1976; "The Thermal Effects of Skeletal Fixation-Pin Insertion in Bone," *JBJS,* 66A:1077, 1984, respectively).

It is proposed that the method in accordance with the present invention, utilizing an oscillating drill, generates less temperature elevation and less thermal damage. The apparatus and method of the present invention also may enable the insertion of K-wires at the same insertional force but lower rotational speeds, or vice versa, in order to reduce temperature elevation during drilling. This may have the beneficial result of causing less complications from thermal damage and a stronger wire holding strength over time.

The following example shows that the wire driver 10 and method of the present invention does not cause surrounding tissue to become wrapped around the wire 16 during insertion, in contradistinction to the prior art rotary drill shown in FIG. 5.

Further, the wire driver 10 and method of the present invention do not cause significant histological changes nor change of neurovascular structure in direct contact with the wire during insertion. This is in direct contrast to marked histological changes and marked vascular spasm of vessels in contact with wires inserted with rotary movement.

While the arc of oscillation may be varied, it has been found that when wire is oscillated, the wire 16 may be inserted through or placed next to gauze, sponges, tendon, and bezels, and even through loose skin and hair, without causing visible damage.

Other advantages of the wire driver 10 are its use in providing guide holes for wire, screw, suture, or cerclage fixation for comminuted fractures. In addition, traction pins and external fixation pins may also be placed more safely, using the method and apparatus of the present invention.

EXAMPLE 1

Hind limbs of two 7.5 Kg New Zealand White rabbits were obtained immediately after killing and stored at 120° C. Prior to testing, the limbs were allowed to thaw to room temperature, and the tibias were disarticulated and stripped of soft tissues. The cortical thickness and diameter of the tibias were found to be consistent with those of adult human metacarpals. To maintain as closely as possible the mechanical properties of fresh living bone, all specimens were kept moistened throughout testing by saline spray.

The proximal and distal ends of each bone were fixed by a screw-clamp device onto a steel U-shaped brace. This holding apparatus was firmly attached to an axial load cell on the platform of an MTS servohydraulic materials testing machine (Instrom).

The drill to be tested was bolted to the fixed crossbar of the Instrom. A traditional rotary drill (Black & Decker) was used for comparison against the prototype oscillating drill (FIG. 1). Drill speed for both instruments was set at 1,200 rpm.

Three different-sized trocar-tipped Kirschner wires (0.028, 0.045, and 0.062 inches in diameter) were evaluated for drilling force (axial load) and holding strength (pull-out force) using the two drill types. The wires were placed such that a 1 cm length projected from the drill bit. the fixed tibial ends were clamped so that the drilled wire penetrated the diaphyseal surfaces perpendicular to the bone's long axis.

To conduct each test, the drill motor was engaged and the Instrom stroke cycle initiated at a constant feed rate of 0.2 cm/sec. The axial load was then continuously graphed on an X-Y recorder. After each trocar point passed through the far cortex, the drill motor and Instrom motions were stopped. Direct, non-rotary, pull-out force was determined by reversal of the Instrom stroke cycle and was recorded as a negative deflection on the X-Y axis recorder.

Figure 7:
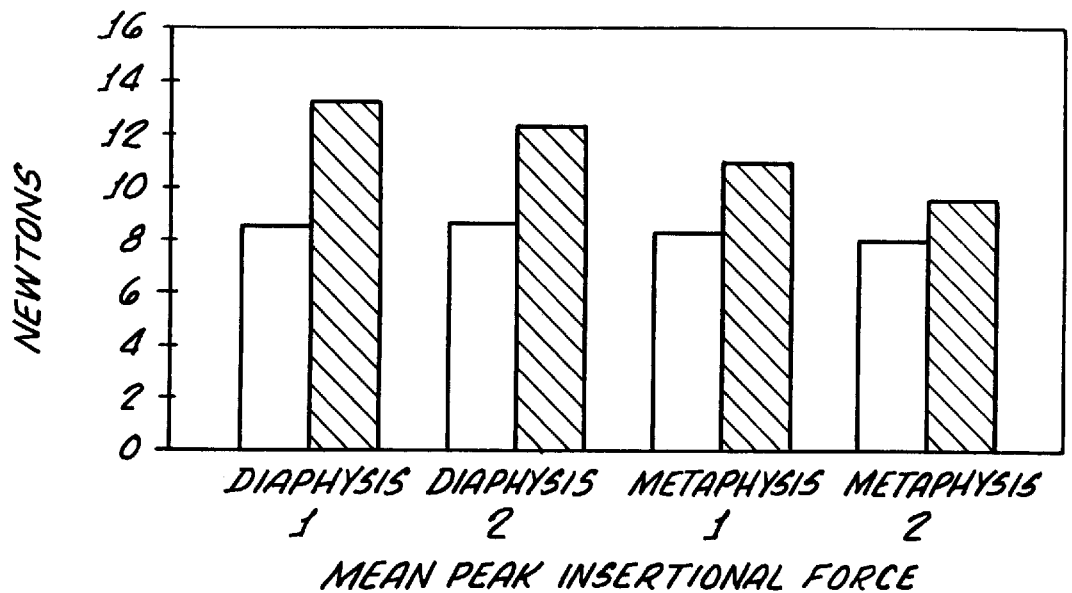
FIG. 7 is a graphic illustration of mean peak insertion force for three different sized K-wires, comparing the oscillating advancement and the force required in the invention vs. the rotary-advance force necessary in prior art devices.
Figure 8:
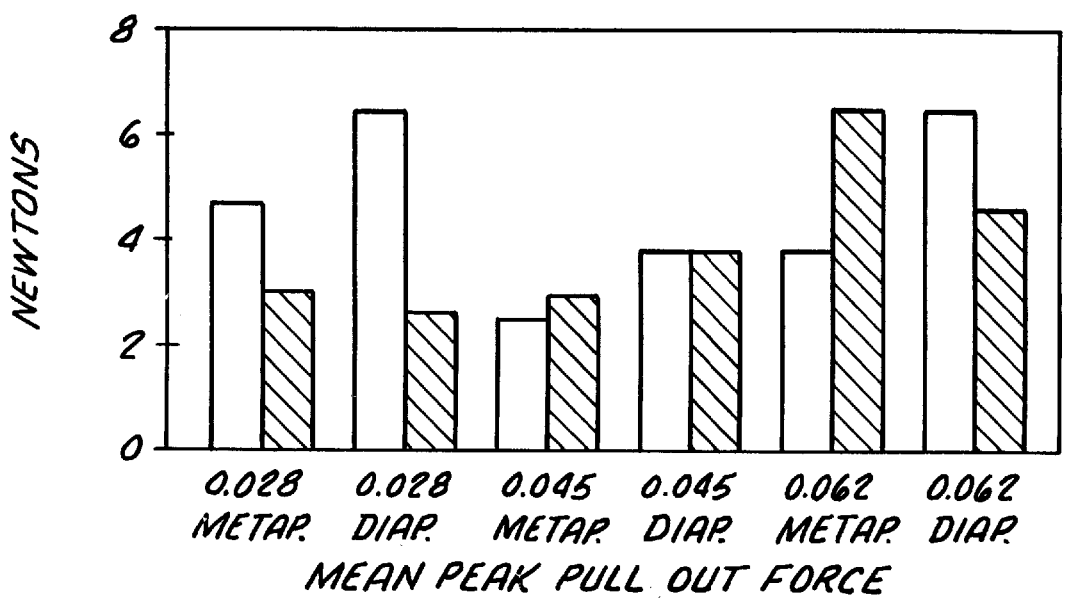
FIG. 8 is a graphic illustration of the mean peak pull-out force for the K-wires inserted, corresponding to FIG. 7, showing that wires inserted by the oscillating method of the present invention, on the average, required more force for removal than wires inserted by conventional rotary method.

Five new K-wires for each size were tested on three tibias using either the rotary or oscillating drill. Each tibia had ten drilled holes, 4 mm apart, equally spaced along the mid-diaphysis. The SAS t-test was used to evaluate the differences in mean peak axial loads and mean peak pull-out forces for thirty point configurations for the two drills.
Results As shown in FIG. 7, the mean peak axial load (insertional force) for the two drill types with respect to all three sized K-wires was significantly different ($P \leq 0.01$). The oscillating drill used an average of 3N less force to penetrate either cortex. As shown in FIG. 8, the mean peak pull-out value was higher for the oscillating drill; however, this higher value does not appear to be statistically significant ($P \leq 0.05$).

EXAMPLE 2

Under standard laboratory conditions, bilateral posterior tibial neurovascular bundles (posterior tibial artery, vein, and nerve) of three male Sprague Dawley Rats (300–350 gm) were isolated following induction of intraperitoneal Pentobarbital anesthesia. Using the oscillating wire driver and a traditional rotary drill on opposite legs, a 0.045 diameter Kirschner wire was placed directly adjacent to the artery and nerve and drilled into the tibia. The wires were placed such that they were in direct contact with both the artery and nerve throughout the drilling process. The wires were then immediately removed. Three days following the procedure, the rats were sacrificed and their posterior tibial vessels and nerve were removed (four specimens in total) and fixed in formalin. All tissue samples were stained with Hematoxylin and Eosin for histologic analysis.
Results The vessels and nerves subjected to the traditional rotary drill were wrapped extensively around the wire during drilling; in addition, one posterior tibial artery was avulsed. Contrariwise, the vessels adjacent to the oscillating wire remained in their anatomical positions, with no discernible movement towards the drilling wire. Light microscopy of the neurovascular bundles in the oscillating wire group revealed normal architecture. In the rotary drill group, the posterior tibial arteries showed extensive histopathological changes characterized by media hypertrophy and marked spasm of the vessel wall.

While a wire driver method and insertion have been hereinabove described in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method of fixating a bone, comprising the steps of:
   oscillating a fixation wire about its longitudinal axis, said wire having cutting means positioned at a first end of said wire;
   advancing said fixation wire into said bone during said oscillating step with a force that is comparatively less than would be required for inserting a rotating wire into said bone;
   Stopping the oscillation of said fixation wire while it is positioned in said bore;
   leaving said fixation wire in said bone while said bone is healing, said fixation wire requiring on average comparatively more force for removal from said bone during said leaving step than would be required for a wire inserted by rotation.

2. A method of fixating a bone, as recited in claim 1, wherein said wire is oscillated at a frequency of about 1200 oscillations per minute.

3. A method of fixating a bone, as recited in claim 1, wherein said one end of said wire has a plurality of discrete cutting edges and said wire is oscillated through an arc equal to or greater than 360 degrees divided by the number of said cutting edges.

4. A method for fixating bone by means of a wire with a cutting means at one end, comprising the steps:
   oscillating said wire at a selected oscillation frequency;
   pressing said one end of said oscillating wire against said bone during said oscillating step with a selected force such that said wire penetrates said bone;
   fixating said bone with said wire, wherein said wire remains in said bone for a period of time sufficient for said bone to heal,
   wherein said cutting means has a plurality of discrete cutting edges and said wire is oscillated through an arc equal to or greater than 360 degrees divided by the number of said cutting edges.

5. A method for fixating bone by means of a wire with a cutting means at one end, comprising the steps:
   oscillating said wire at a selected oscillation frequency of about 1200 oscillations per minute;
   pressing said one end of said oscillating wire against said bone during said oscillating step with a selected force such that said wire penetrates said bone;
   fixating said bone with said wire, wherein said wire remains in said bone for a period of time sufficient for said bone to heal,
   wherein said cutting means has a plurality of discrete cutting edges and said wire is oscillated through an arc equal to or greater than 360 degrees divided by the number of said cutting edges.

* * * * *